US012569697B2

(12) United States Patent
Buchegger et al.

(10) Patent No.: US 12,569,697 B2
(45) Date of Patent: Mar. 10, 2026

(54) DEVICE FOR THE MEDICAL TREATMENT OF HUMANS AND ANIMALS, AND APPLICATION DEVICE FOR SAME

(71) Applicants: LOHMANN & RAUSCHER GMBH, Vienna (AT); RELYON PLASMA GMBH, Regensburg (DE)

(72) Inventors: Patricia Buchegger, Wiener Neustadt (AT); Dominik Burger, Alteglofsheim (DE); Dariusz Korzec, Falkenstein (DE); Stefan Nettesheim, Regensburg (DE); Christian Rohrer, Villach (AT); Florian Hoppenthaler, Parkstetten (DE); Katharina Merz, Neufahrn (DE)

(73) Assignee: Relyon Plasma GmbH, Regensburg (DE)

( * ) Notice: Subject to any disclaimer, the term of this patent is extended or adjusted under 35 U.S.C. 154(b) by 886 days.

(21) Appl. No.: 16/469,922

(22) PCT Filed: Oct. 26, 2017

(86) PCT No.: PCT/EP2017/077499
§ 371 (c)(1),
(2) Date: Sep. 4, 2019

(87) PCT Pub. No.: WO2018/108373
PCT Pub. Date: Jun. 21, 2018

(65) Prior Publication Data
US 2019/0388666 A1     Dec. 26, 2019

(30) Foreign Application Priority Data
Dec. 14, 2016     (DE) .......................... 102016014942.6

(51) Int. Cl.
    *A61M 35/00*     (2006.01)
    *A61N 1/44*      (2006.01)

(52) U.S. Cl.
    CPC ............... *A61M 35/30* (2019.05); *A61N 1/44* (2013.01)

(58) Field of Classification Search
    CPC ... A61M 35/30; A61N 1/44; A61H 2033/141; A61L 2/14
    (Continued)

(56) References Cited

U.S. PATENT DOCUMENTS 8,853,486 B2     10/2014  Wild et al.
9,314,603 B2      4/2016  Kummerfeld et al.
    (Continued)

FOREIGN PATENT DOCUMENTS

DE     102008054401 A1     6/2010
DE     102009019646 A1     11/2010
    (Continued)

OTHER PUBLICATIONS

International Preliminary Report on Patentability dated Jun. 18, 2019 issued in related PCT/EP2017/077499 (13 pgs).

*Primary Examiner* — Andrew J Mensh
(74) *Attorney, Agent, or Firm* — Slater Matsil, LLP

(57)     ABSTRACT

Device for the medical treatment of humans and/or animals, particularly for treating wounds and/or dermatoses, comprising a reactive gas generator designed for generating reactive gases and an application device for applying the reactive gases in a treatment area, comprising a neutralization device designed for neutralizing reactive gases, by means of which the concentration of reactive gases outside the treatment area can be reduced.

15 Claims, 4 Drawing Sheets

(58) Field of Classification Search
USPC .......................................................... 604/23
See application file for complete search history.

(56) References Cited

U.S. PATENT DOCUMENTS

| | | | |
|---|---|---|---|
| 9,498,637 B2 | 11/2016 | Sanders et al. | |
| 10,004,914 B2 | 6/2018 | Nettesheim et al. | |
| 10,143,510 B2 | 12/2018 | Nettesheim et al. | |
| 11,006,995 B2 | 5/2021 | Stieber et al. | |
| 11,752,040 B2 | 9/2023 | Grillitsch et al. | |
| 2003/0187412 A1* | 10/2003 | Martin | A61F 13/8405 604/359 |
| 2011/0288458 A1* | 11/2011 | Jones | A61H 9/0078 601/149 |
| 2014/0249495 A1* | 9/2014 | Mumby | A61M 1/915 604/385.01 |
| 2016/0287310 A1* | 10/2016 | Nettesheim | A61N 1/44 |
| 2016/0296738 A1 | 10/2016 | Suscheck | |
| 2019/0290496 A1* | 9/2019 | Brownhill | A61F 13/00059 |
| 2019/0314535 A1* | 10/2019 | Golkowski | A61L 2/14 |

FOREIGN PATENT DOCUMENTS

| | | | |
|---|---|---|---|
| DE | 102011001416 A1 | 9/2012 | |
| DE | 102012003563 A1 | 8/2013 | |
| DE | 102013113905 A1 | 6/2015 | |
| DE | 102013113941 A1 | 6/2015 | |
| EP | 2636417 A1 | 9/2013 | |
| WO | WO 1998/010825 | 3/1998 | |
| WO | 2011023478 A1 | 3/2011 | |
| WO | 2015184395 A2 | 12/2015 | |

* cited by examiner

250

212

216

240

224

DEVICE FOR THE MEDICAL TREATMENT OF HUMANS AND ANIMALS, AND APPLICATION DEVICE FOR SAME

TECHNICAL FIELD

The invention relates to a device for the medical treatment of humans and/or animals, in particular for the treatment of wounds and/or dermatoses, comprising a reactive gas generator designed for generating reactive gases and an application device for applying the reactive gases in a treatment area as well as an application device for such a device.

BACKGROUND

In therapeutic treatments, in addition to conventional pharmaceutical products and physical treatment approaches, such as compression and/or negative pressure therapy, in recent years, therapeutic approaches are being used, in which reactive gases are used. Corresponding prior art treatment approaches have become known in the areas of dermatology for the treatment of dermatoses and wounds of any type, of oncological diseases as well as in dentistry. During plasma treatment, reactive gas species are formed and purposefully enriched over the treatment area. This represents a possible physical treatment approach. Reactive gases contain highly reactive components. They develop their oxidative potential on the surface, where they oxidize non-selective proteins, lipids, and nucleic acids. Higher eukaryotic cells have highly developed defense mechanisms and can deal with the triggered oxidative stress much better than bacteria, fungi or viruses. These defense mechanisms include, among others, antioxidants, enzymes, such as catalases or dismutases, that break down ROS (Reactive Oxygen Species) as well as the DNA repair mechanisms. Reactive gases are, therefore, particularly suitable and successful in the treatment of wounds and dermatoses.

During plasma treatment, the reactive gases are usually formed by the transfer of sufficient energy in a gas discharge. During such a discharge, a plasma comprising partially or fully charged particles is formed, from which reactive gas species result. Plasma is frequently generated in electrostatic or electromagnetic fields, e.g. by alternating or direct current excitation or microwave excitation. For regenerative medical purposes, cold atmospheric pressure plasmas are commonly used. If air is used as the reactive gas, reactive oxygen and nitrogen species, such as ozone $(O_3)$ and hydrogen peroxide $(H_2O_2)$ or nitrogen oxides, which have a strongly oxidizing effect, primarily develop as products of the plasma. In addition, electrons and ions develop in the plasma per se, too, as well as, emitted during the relaxation of the excited plasma components, photons, which are able to develop an antiseptic and wound healing-promoting effect on their own.

Cold atmospheric pressure plasma can be formed by a dielectrically impeded discharge between electrodes enveloped for insulation, by microwave excitation or by a piezo-electric transformer as an active dielectric in a gas-filled space. In plasma therapy, as a rule, a distinction is made between the following treatment approaches:

1. Direct Plasma Therapy

In this therapeutic approach, the plasma in the treatment or wound area per se is usually generated by means of a dielectrically impeded discharge, during which process the treatment area or the skin can be used as electrode or counter-electrode during plasma generation by means of gas discharge. Devices for direct plasma treatment are, for instance, described in WO2011/023478 and WO2015/184395.

2. Indirect Plasma Therapy

In indirect plasma therapy, the plasma is generated in a separate plasma generator and, via diffusion or, optionally, by means of compressed air, a pump or a blower, conducted to the treatment area. In doing so, the reactive gases generated in the plasma can alternatively be conducted to the treatment area using line segments, such as tubes or the like. Appropriate devices for indirect plasma therapy are described in DE 10 2012 003 563 A1.

In the device described in DE 10 2012 003 563 A1, the reactive gases are generated in a plasma generator arranged in a housing. Using a flow module arranged in the housing, the reactive gases are conveyed to the treatment area in the form of a free jet. For intentional control of the free jet, according to the cited document, a jet control unit comprising a control device controllable by it is provided. This is intended to assure that the gas stream transporting the disinfecting plasma is adjusted in such a way that the plasma will only be active in a locally delimited area, namely in the wound segment to be treated. The surgical staff, who would be exposed to an intolerable long-term constant load in case of wide-spread distribution of the plasma, is supposed to be protected in this way.

In this context, it should be noted that the odor threshold for the ozone formed in the plasma is extremely low and is approximately 15 ppb. The ozone odor is often perceived as very bothersome and unpleasant. Any continuously elevated (much greater than 50 ppb) ozone load may cause coughing as a result of throat irritation, respiratory problems and headaches.

Although, using the open systems for indirect plasma treatment described in the cited document, some protection for the surgical staff can be achieved, it has been shown that the load during plasma treatment is still barely acceptable.

SUMMARY

In view of these problems in the state of the art, the invention is based on the objective of providing a device for the medical treatment of humans and/or animals by means of which, while assuring satisfactory treatment, the load on physicians, nurses, and caregivers using reactive gases, such as ozone, can be reduced. According to the invention, this objective is achieved by a further development of the prior art devices, which is essentially characterized by a neutralization device designed for neutralizing reactive gases, by means of which the concentration of reactive gases outside the treatment area can be reduced.

The invention is based on the realization that neutralization of the reactive gases in medical treatment is done very efficiently and that the remaining concentration of these gases after leaving the treatment area is, as a rule, so low that their neutralization, i.e. their conversion to stable substances, hardly affects the treatment success, but contributes to a significant extent to the relief for physicians, nurses and caregivers.

Devices according to the invention can be used within the scope of both, direct plasma therapy and indirect plasma therapy, optionally utilizing open systems. In any case, the reactive gas generator expediently comprises a plasma source, potentially in the form of an arrangement for generating a dielectrically impeded discharge and/or an ozonizer. In this case, in the direct plasma treatment, the plasma source may be arranged in the immediate vicinity of the treatment area or may even comprise the treatment area, while in the indirect plasma treatment, the reaction generator or the plasma source may be arranged in a separate housing, the reactive gases being conveyed to the treatment area, optionally using compressed air, a pump or a blower.

The neutralization device expediently comprises activated charcoal, which, as a result of its large inner surface, has excellent absorption properties and can be used as pollutant filter. Additionally, the decomposition of ozone is catalyzed according to the following reaction equation: $2\ O_3+C\rightarrow 2\ O_2+CO_2$. Within the scope of the invention, the activated charcoal may alternatively be added to an open cell foam or fleece, which may, if desired, make the passage of the reactive or already partially reacted gases possible. The cells enlarge the inner surface of the neutralization device and, as a result, the effective efficiency factor to increase efficiency.

Moreover, the neutralization device can alternatively be used for adjusting the concentration of the reactive gases in such a way that, although the desired healing or wound healing effect will nevertheless occur, undesired effects can, however, be suppressed or obviated as a result of the mentioned unselective oxidation of proteins, lipids and nucleic acids.

When using an open cell foam blended with activated charcoal, the concentration can be regulated using the cell density and cell size as well as the effective surface. The application device of a device according to the invention may comprise a nozzle device designed for generating a jet of the reactive gases directed at treatment site and is potentially connected to the reactive gas generator using a tube. In this way, the reactive gas is transported to the wound surface in a focused manner. It is formed at the source or in the reactive gas generator and taken to the desired surface using compressed air, a pump or a blower.

The antiseptic and wound-healing promoting effect of the reactive gas is highly concentration-dependent. In an open system, using a nozzle device, the gas species must, therefore, reach the wound surface fast and in a focused manner, in order to prevent any potential diffuse escape. For any homogeneous and large-surface treatment, the wound will be actively scanned using a device according to this embodiment of the invention. In doing so, the use of the nozzle device allows fast non-contact wound treatment.

In this embodiment of the invention, the neutralization device may comprise a housing encircling the jet of reactive gases, preferably widening funnel-like in the direction of the treatment area. Reactive gases that leave the desired treatment volume can thus be effectively neutralized or converted into stable substances, thereby reducing the load on physicians, nurses and caregivers. In this arrangement, the housing may comprise a foam blended with activated charcoal, which is at least partially permeable to the reactive gases. In order to stabilize the neutralization device, on the one hand, and to delimit the treatment volume, on the other hand, the housing, potentially mounted onto the nozzle device, may comprise a plastic funnel that widens in the direction of the treatment area and the outer boundary surface of which is at least partially covered up by the foam that is blended with activated charcoal. In this arrangement, the edge of the foam may extend beyond the edge of the plastic funnel, assuring the neutralizing effect in this way.

The plastic funnel may be designed detachably mountable onto the nozzle device as in a modular structure. In this embodiment of the invention, which is designed for indirect plasma treatment using an open system, the application device may comprise a flow device designed for influencing the flow of the reactive gases, in order to effectively delimit the treatment area in this manner and to supply it with reactive gases.

In another embodiment of the invention, the application device may comprise a covering device for covering the treatment site, in order to define in this manner the treatment volume delimited by the covering device. Although, within the scope of the invention, the use of devices for direct plasma treatment in a closed volume is also conceivable, within the scope of the invention, it has proven to be particularly expedient if devices for indirect plasma treatment are used, in which the covering device comprises at least one inlet port for moving the reactive gases to the treatment site or into the treatment volume and at least one outlet port for removing the reactive gas from the treatment site.

In these closed systems for indirect plasma treatment, the neutralization device may be arranged in the area of the outlet port and preferably cover it. In particularly preferred embodiments of the invention, the covering device may comprise a preferably at least partially water vapor-permeable tubular film, one axial end of which is potentially closed. Such a tubular film or tubular pouch can be pulled over extremities having hard to access and/or large wounds. The reactive gas is generated using an external reactive gas generator, using a plasma source or an ozonizer, for instance, and is introduced into the tube or pouch using compressed air, a pump or a blower. For this purpose, the concentration of the reactive gases, the conditions of the gas introduction, the dimensioning of the outlet port, and the nature of the neutralization device can be adjusted in such a way that the desired healing-promoting effect of the gas, which is highly concentration-dependent, occurs without any excessive side effects. In addition to the accumulation of the gas species, in this arrangement, for efficient treatment, a reactive mass exchange must be assured, which is assured by providing in the tubular film at least one outlet port, preferably two, three or a plurality of outlet ports.

The use of a tubular covering device has the additional advantage that even intact skin will be treated using the reactive gas. In this way, in addition to the wound, the adjacent skin areas are disinfected and vasodilation, by NO for instance, be triggered on the entire extremity.

As is obvious from the explanation above, in a preferred embodiment of the invention, the covering device may be designed like a type of limb bag, a sock, a glove, a vest, or a trouser. For manufacturing the tubular film, a material that is at least partially water-vapor permeable can be used, as described for example in EP 12 002 332.0.

The covering device, designed, for example, in the form of a tubular film, may be attachable to the skin in the region of a fastening edge. For this purpose, a closure strip and/or an adhesive, such as a self-adhesive film, will preferably be provided.

For uniform treatment covering a major surface, the application device may comprise a distribution layer designed for distributing the reactive gases over a specified surface. This distribution layer may, for example, be embodied according to DE 10 2009 019 646. In the embodiments of the invention described above, which are designed for indirect plasma treatment, the reactive gas generator will expediently be connected to an inlet port of the application device using a tube. The outlet port may alternatively be integrated in the form of an additional tube lumen in the tube, in a connector for the tube and/or in the fastening edge. If the application device is embodied in the form of a patch or a wound dressing, the covering device may comprise an occlusive film, which is attachable to the skin in the region of a fastening edge that encircles the treatment area. Fastening may alternatively be accomplished using an open cell foam edge, which is blended with activated charcoal and forms a neutralization device. In this case, the foam edge forms a plurality of outlet ports.

During embodiment of the application device as a wound dressing, the covering device may, in addition to the occlusive film, comprise a foam, a superabsorber and/or a fleece. In the case of heavily exuding wounds, reflux of the exudates into the tube used for introducing the reactive gases must be prevented. The tube must be sealed in sterile form to assure that the next treatment is safe. Wounds in their granulation phase excrete a large amount of exudate, primarily comprising dead cells, bacteria, and protein. Precautions for the inlet and outlet ports of the reactive gas must be taken, in order to prevent the penetration of the exudate and other fluids. Such a precaution may be the use of a flap valve or varying surface coatings.

If the patch, which is designed for introducing the reactive gases, remains on the wound for an extended period of time, the tube used to introduce the reactive gases may be made of more flexible materials and may, for example, comprise a tubular film. The unstable material prevents pressure points and increases the wearing comfort for the patient.

If a device according to the invention comprises an arrangement embodied as a patch, the covering device may comprise a preferably gas-permeable, in particular film-like, adhesive layer, which forms its outer boundary surface that faces away from the treatment area and optionally forms a fastening edge, which encircles the treatment area, covers the open-cell foam, which is blended with activated charcoal and encircles on the side facing away from the treatment area.

Adequate treatment of chronic wounds caused by venous or arterial problems, such as venous, arterial or mixed Ulcus cruris, in many cases also comprises compression therapy in addition to the plasma therapy. For treatment using reactive gases under the compression dressing without any pressure pain, in this case, the gas will be introduced via a thin tube or a tubular film. The tube is flexible and prevents pressure pain. The tubular film can be designed in dimensionally more stable form by using a support, for example a foam. In order to assure the dynamic mass exchange at the boundary layer, the embodiment variants of devices according to the invention having a wound dressing, in particular if they comprise a self-adhesive edge, or if compression dressings are applied, must be provided with one or a plurality of outlet ports. For this purpose, similar to the inlet port, the outlet port may comprise a thin flexible tube or similar. In this case, the neutralization device can be directly integrated into the outlet tube.

BRIEF DESCRIPTION OF THE DRAWINGS

The invention will be explained hereinafter with reference to the drawing, to which reference is expressly made with respect to all details that are essential to the invention and are not specifically highlighted in the description. The drawing shows the following.

DETAILED DESCRIPTION OF ILLUSTRATIVE EMBODIMENTS

Figure 1:
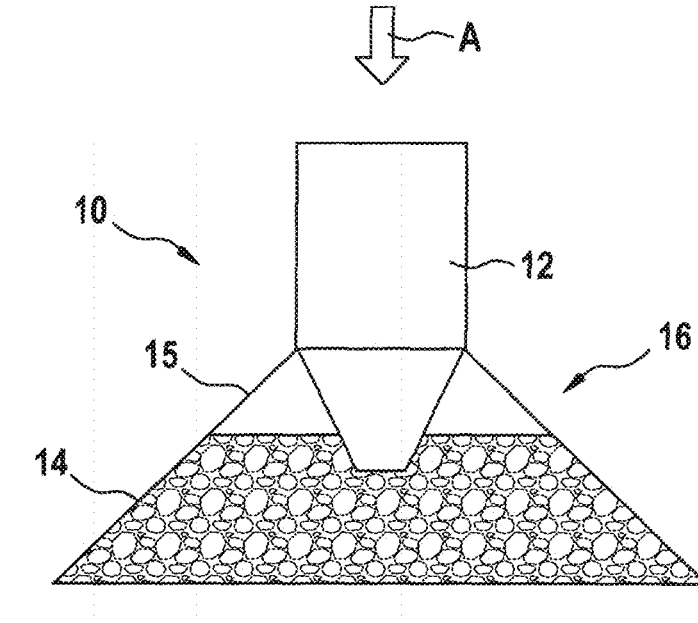
FIG. 1 a treatment device according to a first embodiment of the invention.

The treatment device illustrated in FIG. 1 comprises a nozzle device 12, to which reactive gases from a reactive gas generator embodied in the form of a plasma source are conducted, as indicated by the arrow A. Using nozzle unit 12, the reactive gases are conveyed to the wound surface in the form of an open gas jet. To nozzle device 12, a funnel-shaped gas conduction device is mounted. Nozzle device 12 and gas conduction device 16 together form an application device in accordance with the invention.

The gas conduction device comprises a plastic funnel 15 that widens in the direction of the wound to be treated and, at its outer boundary surface, is covered by an open cell foam 14 that is provided with activated charcoal, the open cell tube 14 extending beyond the edge of plastic funnel 15 in the direction of the wound. Using the open cell foam, which is blended with activated charcoal, the reactive gases leaving the treatment area are neutralized, i.e. converted to stable substances. Ozone, for example, is converted to oxygen and carbon dioxide using activated charcoal.

Figure 2:
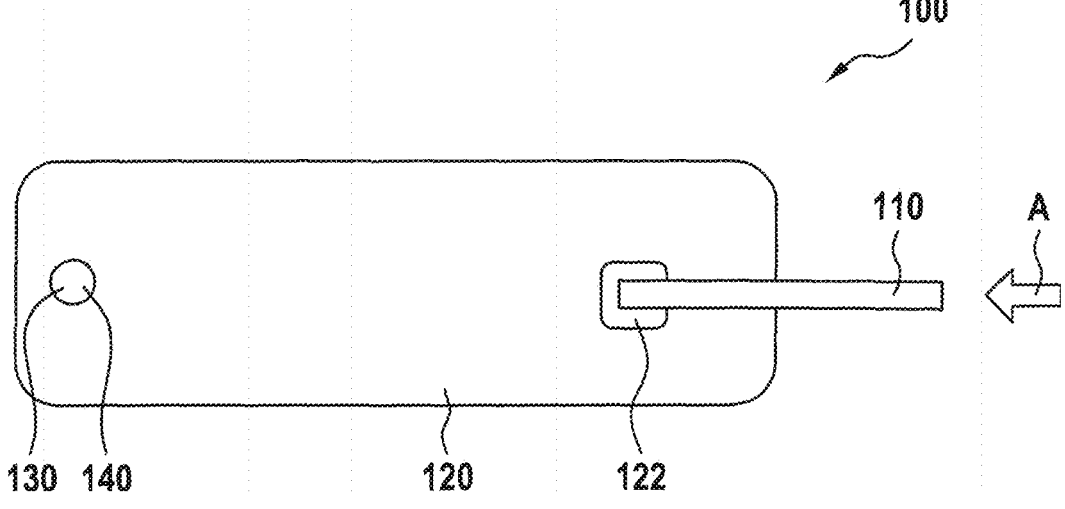
FIG. 2 a treatment device according to a second embodiment of the invention.

In the embodiment of the invention illustrated in FIG. 2, the reactive gases produced in a reactive gas generator in the form of a plasma source, as indicated by arrow A, are introduced into a tubular film pouch 120 using a tube 110. In this arrangement, onto tubular film pouch 120, an adapter 122 is mounted, to which tube 110 will be connected.

For efficient treatment of a wound, dermatosis or the like of an extremity placed into a tubular film pouch 120, a dynamic mass exchange must be assured, during which the introduced and reacted reactive gases, are continuously replaced by freshly supplied reactive gases. For this purpose, tubular film pouch 120 comprises an outlet port 130 designed for carrying the possibly already reacted reactive gases away from the treatment site and covered by an activated charcoal filter 140 that serves as neutralization device.

Tubular film pouch 120 may be made of water-vapor permeable film, as described in EP 12 002 332.0, for example.

Figure 3:
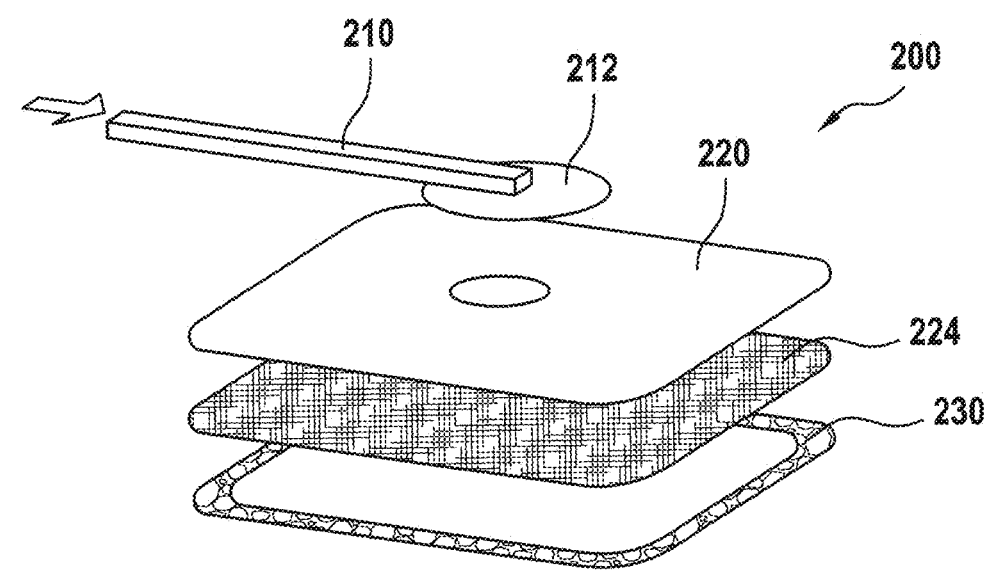
FIG. 3 a treatment device according to a third embodiment of the invention.

In FIG. 3, a treatment device 200 according to the invention is illustrated in the form of a patch designed for the local treatment of wounds, delimited toward the outside, using reactive gases in a relatively tight system. The reactive gas will be conducted to the wound to be treated by a plasma source using a tube 210, an adapter 212, and a distribution zone 224. Adapter 212 is mounted gas-tight onto an occlusive film 220, in the region of adapter 212, the occlusive film 220 having an inlet port, through which the reactive gas, passing through distribution film 224, can reach the wound to be treated. Distribution zone 224 may be embodied according to the state of the art in accordance with DE 10 2009 019 646.

At the boundary surface of distribution film 224, which faces the wound, an open cell activated carbon foam encircling the edge of film 220 is arranged, by way of which film 220 can be fastened to the skin surrounding the wound.

Through the open cell charcoal foam, the reactive gases, delivered using tube 210 and film 220, can leave the treatment area again and be neutralized subject to the effect of the activated charcoal in such a way that physicians and nurses, and caregivers are not exposed to any loads as a result of the reactive gases.

Figure 4:
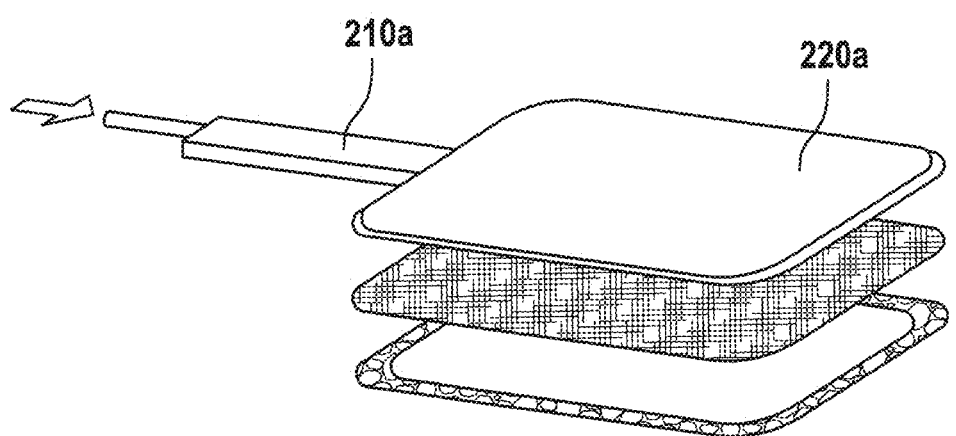
FIG. 4 an additional treatment device according to a fourth embodiment of the invention, FIG. 5 a treatment device according to a fifth embodiment of the invention, FIG. 6 a treatment device according to a sixth embodiment of invention, and FIG. 7 the efficiency factor of the neutralization device in an embodiment.

The embodiment of the invention illustrated in FIG. 4 essentially differs from the embodiment explained on the basis of FIG. 3 in that, instead of the occlusive film 220, a wound dressing 220*a* is used, which may contain a foam, a superabsorber, a fleece or similar. In the embodiment of the invention illustrated in FIG. 4, the reactive gases are introduced using a tubular film 210*a*.

Figure 5:
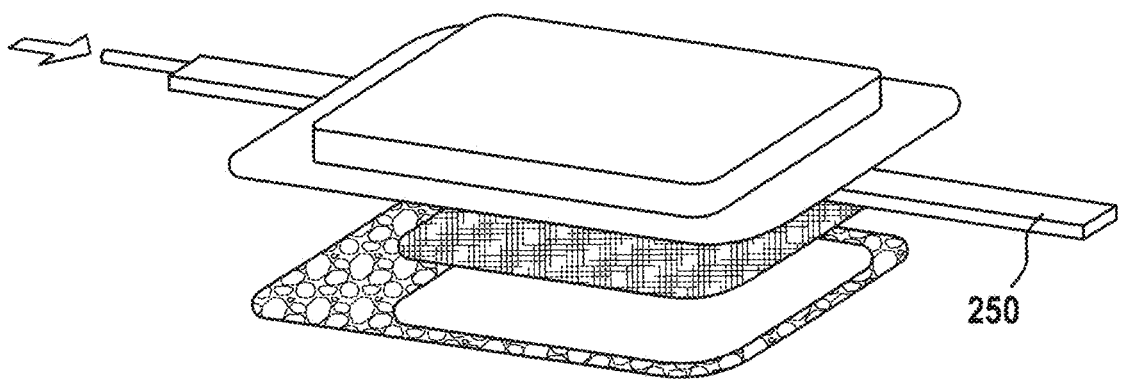

The embodiment of the invention illustrated in FIG. 5 differs from the embodiment explained with reference to FIG. 4 in that, in addition to the open cell activated charcoal foam, for the reactive gases, a flexible outlet tube is provided, in which an activated charcoal filter may be integrated, in order to neutralize the reactive gases there, too.

Figure 6:
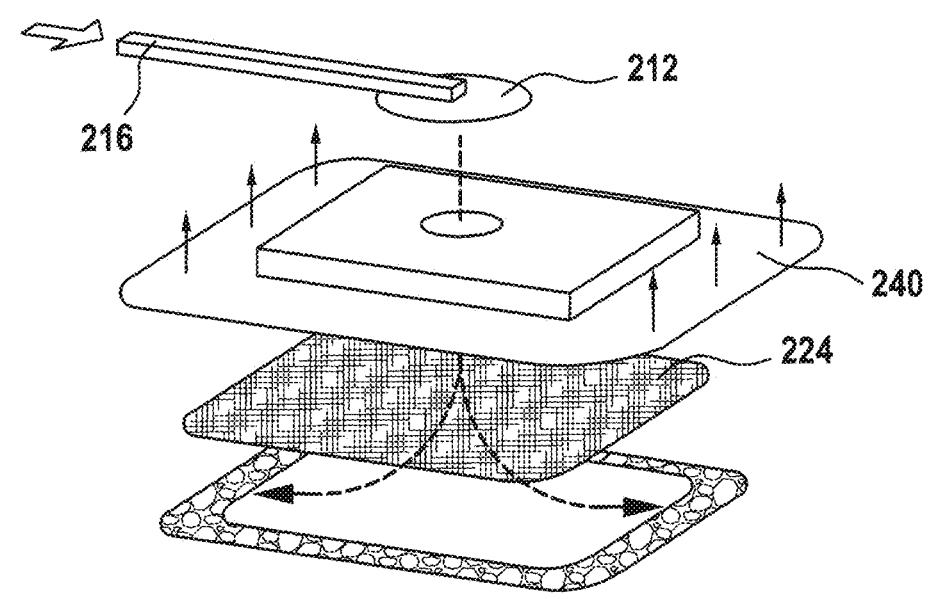

The embodiment of the invention illustrated in FIG. 6 comprises, in addition to the components explained with reference to FIG. 4, an adhesive layer embodied as adhesive film 240. The adhesive layer forms the outer boundary surface of the covering device, facing away from the treatment area.

It is made of a gas-permeable material. Using the adhesive layer, foam blended with activated charcoal is covered. In this embodiment, the adhesive layer extends beyond the activated charcoal-containing foam edge and encircles this foam edge on the side facing away from the treatment area. On the boundary surface, on the skin side with respect to the outer boundary surface, the adhesive layer is adhesively embodied and can be fastened to the skin encircling the activated charcoal-containing foam, in order to fasten in this manner the entire covering device 70 to the skin encircling the treatment area. In the embodiment of the invention illustrated in FIG. 6, similar to the embodiment illustrated based on FIG. 3, the reactive gas is delivered to the wound to be treated from a plasma source by way of a tube 210, an adapter 212 and a distribution zone 224.

Figure 7:
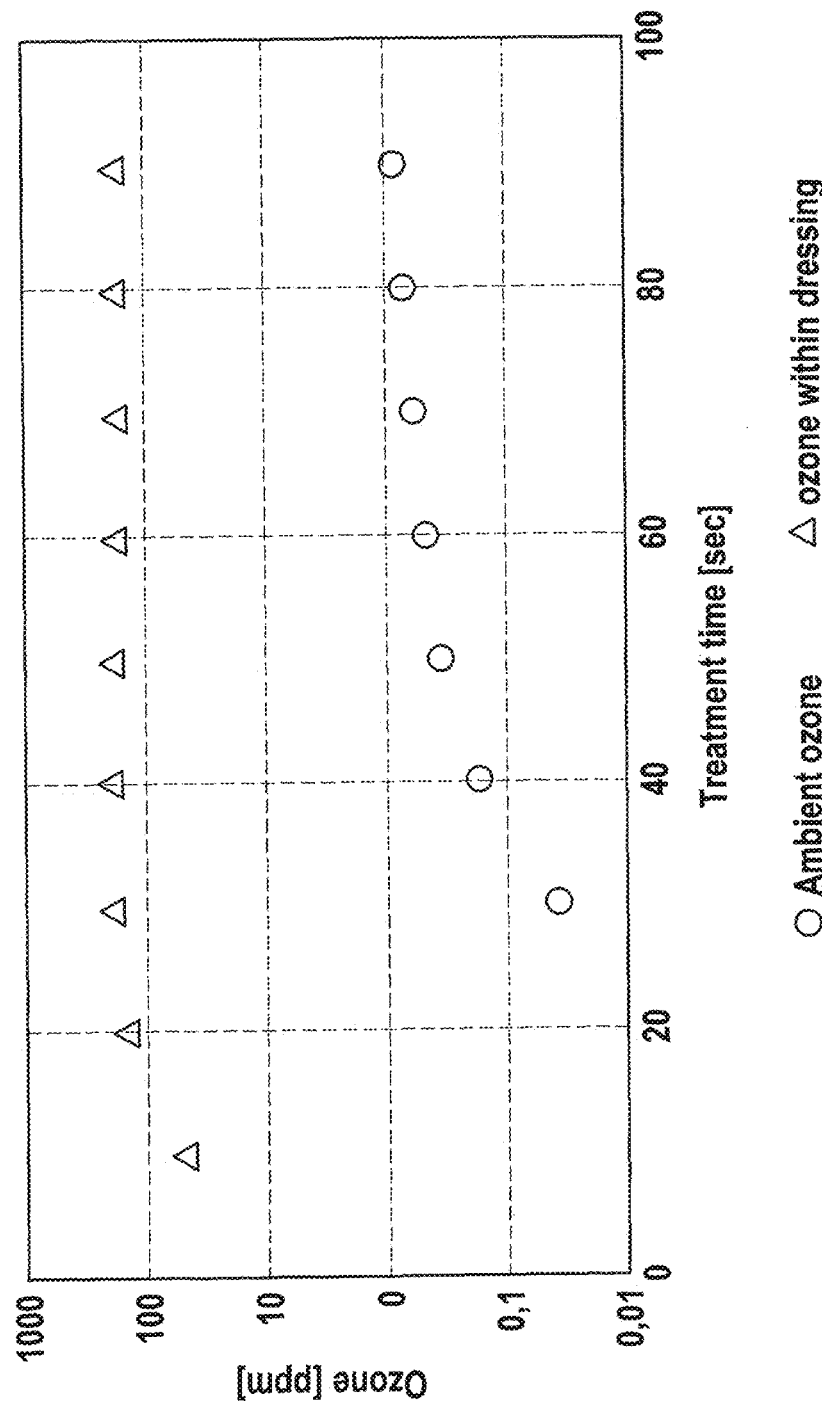

FIG. 7 shows the ozone concentration curve illustrated in an embodiment as in FIG. 3. In this embodiment, the neutralization device is embodied as a 1.25 cm foam edge blended with activated charcoal and integrated in this way in the wound dressing, which is fastened over the wound. The reactive species, such as ozone for example, are filtered and neutralized by the open cell foam. In doing so, the ozone concentration above the wound surface increases to approx. 200 ppm, while the ambient ozone concentration in a defined volume of 36 $dm^3$ increases without any air circulation increases by a slope of 0.008 ppm. The neutralization device in this embodiment, comprising an effective area of 0.6 $cm^3$, has an efficiency factor of 99.75%.

The invention is not limited to the embodiments explained with reference to the drawing. In fact, the use of devices according to the invention for direct plasma treatment is also conceivable. Other types of reactive gases can be used. The application device can be randomly adjusted to the shape of the wounds and the anatomical conditions.

The invention claimed is:

1. A device comprising:
a reactive gas generator designed for generating reactive gases; and
a patch designed for local treatment of wounds, delimited toward an outside, wherein the patch includes at least one inlet port configured for introducing the reactive gases, wherein a covering device of the patch is selected from the group consisting of an occlusive film, a distribution film, and combinations thereof,
wherein an open cell foam blended with activated charcoal encircles a fastening edge of the patch and a treatment area to thereby reduce a concentration of the reactive gases outside of the treatment area, and
wherein the treatment area is enclosed by the fastening edge, wherein the open cell foam does not cover the treatment area.

2. The device of claim 1, wherein the patch comprises at least one outlet port configured for removing the reactive gases from the treatment area.

3. The device of claim 2, wherein the open cell foam blended with activated charcoal is arranged in the treatment area, which covers the outlet port.

4. The device of claim 1, wherein the fastening edge of the covering device is fastenable to skin.

5. The device of claim 4, wherein the fastening edge comprises an adhesive layer embodied as an adhesive film, and wherein the adhesive layer forms an outer boundary surface of the covering device that faces away from the treatment area.

6. A treatment kit for fabricating the device of claim 1, the treatment kit comprising:
the patch and the open cell foam blended with activated charcoal.

7. The device of claim 1, wherein the covering device is a covering film, and wherein the covering film is the occlusive film.

8. The device of claim 7, wherein the at least one inlet port is connected to an adapter, which is mounted gas-tight onto the occlusive film.

9. The device of claim 7, wherein the covering device further comprises a foam, a superabsorber, a fleece, or combinations thereof.

10. The device of claim 2, wherein the reactive gases are introducible in the treatment area via the inlet port using a tubular film.

11. The device of claim 5, wherein the adhesive layer comprises a gas-permeable material.

12. The device of claim 1, wherein the concentration of the reactive gases is regulated by a cell density, a cell size and an effective surface of the open cell foam blended with activated charcoal.

13. A device comprising:
a reactive gas generator designed for generating reactive gases; and
a patch designed for local treatment of wounds, delimited toward an outside, wherein the patch includes at least one inlet port configured for introducing the reactive gases,
wherein a covering device of the patch is selected from the group consisting of an occlusive film, a distribution film, and combinations thereof,
wherein an open cell foam blended with activated charcoal encircles a fastening edge of the patch and a treatment area, and
wherein the treatment area is enclosed by the fastening edge, wherein the open cell foam does not cover the treatment area.

14. The device of claim 13, wherein a concentration of the reactive gases is regulated by a cell density, a cell size and an effective surface of the open cell foam blended with activated charcoal.

15. A device comprising:

a reactive gas generator designed for generating reactive gases; and a patch designed for local treatment of wounds, delimited toward an outside, wherein the patch includes at least one inlet port configured for introducing the reactive gases, wherein a covering device of the patch is selected from the group consisting of an occlusive film, a distribution film, and combinations thereof, wherein an open cell foam blended with activated charcoal encircles a fastening edge of the patch and a treatment area, wherein the open cell foam is frame-shaped, and wherein an inner area of the frame is free of the open cell foam.

* * * * *